US012569144B2

(12) United States Patent (10) Patent No.: US 12,569,144 B2
Zhao (45) Date of Patent: Mar. 10, 2026

(54) ACOUSTIC IMAGING AND MEASUREMENTS USING WINDOWED NONLINEAR FREQUENCY MODULATION CHIRP

(71) Applicant: DEEPSIGHT TECHNOLOGY, INC., Los Altos, CA (US)

(72) Inventor: Danhua Zhao, San Jose, CA (US)

(73) Assignee: DEEPSIGHT TECHNOLOGY, INC., Santa Clara, CA (US)

(*) Notice: Subject to any disclaimer, the term of this patent is extended or adjusted under 35 U.S.C. 154(b) by 0 days.

(21) Appl. No.: 18/280,200

(22) PCT Filed: Mar. 2, 2022

(86) PCT No.: PCT/US2022/018515
§ 371 (c)(1),
(2) Date: Sep. 1, 2023

(87) PCT Pub. No.: WO2022/187357
PCT Pub. Date: Sep. 9, 2022

(65) Prior Publication Data
US 2024/0138681 A1     May 2, 2024

Related U.S. Application Data

(60) Provisional application No. 63/156,782, filed on Mar. 4, 2021.

(51) Int. Cl.
*A61B 5/00* (2006.01)
*G01S 7/52* (2006.01)
(52) U.S. Cl.
CPC ........ *A61B 5/0097* (2013.01); *G01S 7/52019* (2013.01); *G01S 7/52031* (2013.01); *G01S 7/52044* (2013.01)

(58) Field of Classification Search
CPC .............. A61B 5/0097; G01S 7/52019; G01S 7/52031; G01S 7/52026; G01S 15/8961
See application file for complete search history.

(56) References Cited

U.S. PATENT DOCUMENTS

| 4,673,941 A | 6/1987 | Van Der Mark |
| 5,224,482 A | 7/1993 | Nikoonahad et al. |
| (Continued) | | |

FOREIGN PATENT DOCUMENTS

| JP | 2000300550 A | 10/2000 |
| JP | 2002272737 A | 9/2002 |
| (Continued) | | |

OTHER PUBLICATIONS

"Three-Dimensional Ultrasonic Needle Tip Tracking with a Fiber-Optic Ultrasound Receiver" by W. Xia et al. J Visualized Ex. (Year: 2018).*

(Continued)

*Primary Examiner* — Jason M Ip
(74) *Attorney, Agent, or Firm* — Kilpatrick Townsend & Stockton LLP

(57) ABSTRACT

A method for performing acoustic imaging and measurements may include generating a nonlinear frequency modulation (NLFM) chirp waveform based on a frequency response of at least one transducer. The method may further include generating an apodized signal by applying a window function to the NLFM chirp waveform. The method may further include exciting the at least one transducer with the apodized signal. The method may further include compressing received signals by using one or more matched filters.

30 Claims, 12 Drawing Sheets

1200

(56)                References Cited

U.S. PATENT DOCUMENTS

| | | | |
|---|---|---|---|
| 5,938,611 | A | 8/1999 | Muzilla et al. |
| 10,674,999 | B2 | 6/2020 | Pekar et al. |
| 10,677,901 | B2 | 6/2020 | Lee et al. |
| 2002/0117004 | A1* | 8/2002 | Satoh ................. G01S 7/52044 73/628 |
| 2007/0038108 | A1* | 2/2007 | Hao ........................ A61B 8/06 600/454 |
| 2008/0130413 | A1 | 6/2008 | Bachelor et al. |
| 2013/0102865 | A1 | 4/2013 | Mandelis et al. |
| 2017/0299704 | A1 | 10/2017 | Rothberg et al. |
| 2018/0154394 | A1 | 6/2018 | Haque et al. |
| 2019/0129026 | A1* | 5/2019 | Sumi ....................... A61B 6/00 |

FOREIGN PATENT DOCUMENTS

| | | | |
|---|---|---|---|
| JP | 2005081150 | A | 3/2005 |
| JP | 2009053031 | A | 3/2009 |
| JP | 2010043958 | A | 2/2010 |
| JP | 2010243295 | A | 10/2010 |
| JP | 2011038948 | A | 2/2011 |
| JP | 2011237338 | A | 11/2011 |
| JP | 2012194043 | A | 10/2012 |
| WO | 0121074 | A1 | 3/2001 |

OTHER PUBLICATIONS

"Synthetic Aperture Radar Imaging Using Nonlinear Frequency Modulation Signal" by J. Saeedi et al. IEEE Trans Aero Elect Syst. 2016.*

"A range estimation system using coded ultrasound" by R. Carotenuto. Sensors and Actuators. 238, pp. 104-111, 2016.*

US International Search Report and Written Opinion for PCT/ US2022/018515 mailed Jun. 3, 2022.

Zhang et al., "A Novel NLFM Waveform With Low Sidelobes Based on Modified Chebyshev Window", https://ieeexplore.ieee. org/document/8809195, May 5, 2020; pp. 814-818.

Monifi, et al., "Ultrasound Sensing Using a Fiber Coupled Silica Microtoroid Resonator Encapsulated in a Polymer", 2013 IEEE Photonics Conference, Bellevue, WA, USA, doi: 10.1109/IPCon. 2013.6656511, 2013, pp. 2015-2016.

PCT/US2022/018515, "International Preliminary Report on Patentability", Sep. 14, 2023, 25 pages.

Wei, et al., "High-Frequency Ultrasonic Sensor Arrays Based on Optical Micro-ring Resonators", Proc. SPIE 10600, Health Monitoring of Structural and Biological Systems XII, 1060003, Mar. 27, 2018, 8 pages.

European Extended Search Report and Opinion for EP 22763974.7 mailed Dec. 10, 2024.

Gran et al., "P2F-6 Designing Non-Linear Frequency Modulated Signals For Medical Ultrasound Imaging", 2006 IEEE Ultrasonics Symposium, Oct. 1, 2006; pp. 1714-1717.

Sabatini et al. "Digital-Signal-Processing Techniques For The Design of Coded Excitation Sonar Ranging Systems", Proceedings of the 1996 International Conference on Robotics And Automation, vol. Conf. 13, Apr. 22, 1996; pp. 335-340.

Kåsine, et al., "Needle tip tracking for ultrasound-guided peripheral nerve block procedures—An observer blinded, randomised, controlled, crossover study on a phantom model", Acta Anaesthesiologica Scandinavica 63.8 (2019): 1055-1062.

Mari, et al., "Needle-tip localization using an optical fibre hydrophone", Optical Fibers and Sensors for Medical Diagnostics and Treatment Applications XIV. vol. 8938. SPIE, 2014.

Xia, et al., "Coded excitation ultrasonic needle tracking: An in vivo study", Medical physics 43.7 (2016): 4065-4073.

JP2023-553294, "Office Action", Jan. 6, 2026, 16 pages.

* cited by examiner

200

Generate a nonlinear frequency modulation (NLFM) chirp
waveform based on a frequency response of at least one
transducer
201

Generate an apodized signal by applying a window function
to the NLFM chirp waveform
202

Excite the at least one transducer with the apodized signal
203

ACOUSTIC IMAGING AND MEASUREMENTS USING WINDOWED NONLINEAR FREQUENCY MODULATION CHIRP

CROSS-REFERENCE TO RELATED APPLICATIONS

This application is a National Stage Application of PCT Application No. PCT/US2022/018515, filed Mar. 2, 2022, which claims the benefit of and priority to U.S. Patent App No. 63/156,782, filed on Mar. 4, 2021. Each of these applications is hereby incorporated by reference in their entireties for all purposes.

TECHNICAL FIELD

The present disclosure generally relates to the field of acoustic imaging, and in particular to methods and devices that improve an ultrasound image quality using windowed nonlinear frequency modulation chirp.

BACKGROUND

Acoustic imaging is used in various industries including medical imaging and medical diagnosis due to a number of advantages. For example, ultrasound sensing uses ultrasound signal which has a remarkable penetration depth. Moreover, ultrasound imaging is known to be an advantageously non-invasive form of imaging, as it is based on non-ionizing radiation.

Image quality of ultrasound imaging systems is often determined by imaging parameters such as, for example, axial resolution. The axial resolution parameter depends in part on the bandwidth of the ultrasound transducer. In general, axial resolution is linearly proportional to bandwidth. In various known ultrasound imaging methods and systems, the bandwidth of the ultrasound transducer imposes a fundamental limit on the system imaging bandwidth. However, the typical bandwidth of a PZT transducer is often at 70% to 80% relative bandwidth, which limits the optimal axial resolution and thus image quality that can be achieved using the various known ultrasound methods and systems. Thus, there is a need for methods and devices for improving ultrasound image quality.

SUMMARY

In some variations, a method for performing acoustic imaging may include generating a nonlinear frequency modulation (NLFM) chirp waveform based on a frequency response of at least one transducer (e.g., a piezoelectric sensor, a single crystal material sensor, a piezoelectric micromachined ultrasound transducer (PMUT), a capacitive micromachined ultrasonic transducer (CMUT) sensor, and/or the like). The method may further include generating an apodized signal by applying a window function (e.g., a Gaussian window function or a Kaiser window function) to the NLFM chirp waveform. The method may further include exciting the at least one transducer with the apodized signal (e.g., performed by a multi-level voltage transmitter). A signal generated based on the NLFM chirp waveform may introduce at least one sidelobe having a magnitude, while the window function may reduce the magnitude of (e.g., reduce to zero or eliminate) the at least one sidelobe introduced by the NLFM chirp waveform.

In some variations, the method may further include transmitting an acoustic signal based on the apodized signal. The acoustic signal may be transmitted using the at least one transducer. The transmitted acoustic signal may have a higher bandwidth (e.g., 120%) than the intrinsic bandwidth of the at least one transducer.

In some variations, the method may further include receiving a set of echo signals in response to transmitting the acoustic signal. The method may further include generating a set of imaging signals based on the set of echo signals. The set of echo signals may be received and the set of imaging signals may be generated by the at least one transducer. In some implementations, the set of echo signals may be received and the set of imaging signals may be generated by using at least one optical sensor (e.g., a whispering gallery mode optical sensor, an integrated photonic circuit based optical sensor, and/or the like). When using the at least one optical sensor, generating the set of imaging signals may further involve converting the set of echo signals to a set of optical signals, and generating the set of imaging signals based on the set of optical signals.

In some variations, the method may further include delaying one or more imaging signals of the set of imaging signals using one or more respective delay units. Each delay unit from the one or more respective delay units may be based on a depth associated with the imaging signal to be delayed by the delay unit. The method may further include summing the set of imaging signals to produce an output signal. The method may further include, after summing the set of imaging signals, correlating the output signal with the NLFM chirp waveform using a matched filter, to produce a compressed output signal. The method may further include, before summing the set of imaging signals, correlating each of the set of imaging signals with the NLFM chirp waveform using a respective matched filter to produce compressed imaging signals. Summing the set of imaging signals may involve summing the compressed imaging signals using an adder to produce the output signal.

Excitation of the at least one transducer with the apodized signal may increase one or more of an axial resolution, a contrast resolution, and a signal-to-noise ratio of an ultrasound image generated based on the set of imaging signals. In some variations, the NLFM chirp waveform or the window function may be predetermined prior to performing the acoustic imaging. On the other hand, in some variations, the NLFM chirp waveform or the window function may be dynamically adjusted while performing the acoustic imaging.

In some variations, the NLFM chirp waveform may be generated based on a function that is non-decreasing, positive, and continuous. The frequency function of the NLFM chirp waveform may increase monotonically. The function may, for example, be of the form $f(t)=c\ a\ \tan(a\ (t-b))+d$, where a $\tan(\cdot)$ is an arctangent function, t is time, a is a scaling parameter, b is a shift control parameter, c is a frequency range control parameter, and d is an initial minimum frequency parameter. In some variations, the NLFM chirp waveform may be generated based on a polynomial function. Yet in some other variations, the NLFM chirp waveform may be generated based on a look up table.

In some variations, the method may include amplifying the apodized signal before exciting the at least one transducer. Transmit aperture apodization can reduce sidelobes of an acoustic beam. The aperture apodization may be realized by using a set of preset gain parameters for individual transmit channels.

In some variations, a method for performing one or more acoustic measurements (e.g., distance) may include generating a nonlinear frequency modulation (NLFM) chirp waveform based on a frequency response of at least one transducer (e.g., a piezoelectric sensor, a single crystal material sensor, a piezoelectric micromachined ultrasound transducer (PMUT), a capacitive micromachined ultrasonic transducer (CMUT) sensor, and/or the like). The method may further include generating an apodized signal by applying a window function (e.g., a Gaussian window function or a Kaiser window function) to the NLFM chirp waveform. The method may further include exciting the at least one transducer with the apodized signal (e.g., performed by a multi-level voltage transmitter). A signal generated based on the NLFM chirp waveform may introduce at least one sidelobe having a magnitude, while the window function may reduce the magnitude of (e.g., reduce to zero or eliminate) the at least one sidelobe introduced by the NLFM chirp waveform.

In some variations, the method may further include transmitting an acoustic signal based on the apodized signal. The acoustic signal may be transmitted using the at least one transducer. The transmitted acoustic signal may have a higher bandwidth (e.g., 120%) than the intrinsic bandwidth of the at least one transducer.

In some variations, the method may further include receiving a set of received acoustic signals in response to transmitting the acoustic signal. The method may further include generating a set of measurement signals based on the set of received acoustic signals. The set of received acoustic signals may be received by and the set of measurement signals may be generated by at least one sensor such as a second transducer different (separate) from the excited transducer. In some implementations, the sensor may be an optical sensor, as the set of received acoustic signals may be received by and the set of measurement signals may be generated by using at least one optical sensor (e.g., a whispering gallery mode optical sensor, an integrated photonic circuit based optical sensor, and/or the like). When using the at least one optical sensor, generating the set of measurement signals may further involve converting the set of received acoustic signals to a set of optical signals, and generating the set of measurement signals based on the set of optical signals.

The method may include correlating at least one of, or each of, the set of measurement signals with the NLFM chirp waveform using a respective matched filter to produce compressed measurement signals.

In some variations, the NLFM chirp waveform or the window function may be predetermined prior to performing the acoustic measurements. On the other hand, in some variations, the NLFM chirp waveform or the window function may be dynamically adjusted while performing the acoustic measurements.

In some variations, the NLFM chirp waveform may be generated based on a function that is non-decreasing, positive, and continuous. The frequency function of the NLFM chirp waveform may increase monotonically. The function may, for example, be of the form $f(t)=c$ a $\tan(a\ (t-b))+d$, where a $\tan(\cdot)$ is an arctangent function, t is time, a is a scaling parameter, b is a shift control parameter, c is a frequency range control parameter, and d is an initial minimum frequency parameter. In some variations, the NLFM chirp waveform may be generated based on a polynomial function. Yet in some other variations, the NLFM chirp waveform may be generated based on a look up table.

DETAILED DESCRIPTION

Non-limiting examples of various aspects and variations of the invention are described herein and illustrated in the accompanying drawings.

Axial resolution of medical ultrasound imaging systems is often limited by transducer bandwidth. The method and systems of acoustic imaging described herein may overcome such axial resolution limitations by exciting ultrasound transducers with nonlinear frequency modulation (NLFM) chirp waveforms. Resulting transmitted acoustic signals based on the NLFM chirp waveforms shown and described herein demonstrate significantly higher bandwidth than intrinsic bandwidth of transducers. Moreover, the NLFM chirp waveform may be apodized by a window function to reduce range sidelobe levels introduced by the chirp waveforms. Echo signals received in response to the transmitted acoustic signals, which are generated based on the NLFM chirp waveform and the window function, may be correlated with the same NLFM chirp pulses to compress the signal width to produce final ultrasound images with superior axial resolution, contrast resolution, and signal-to-noise ratio.

Figure 6:
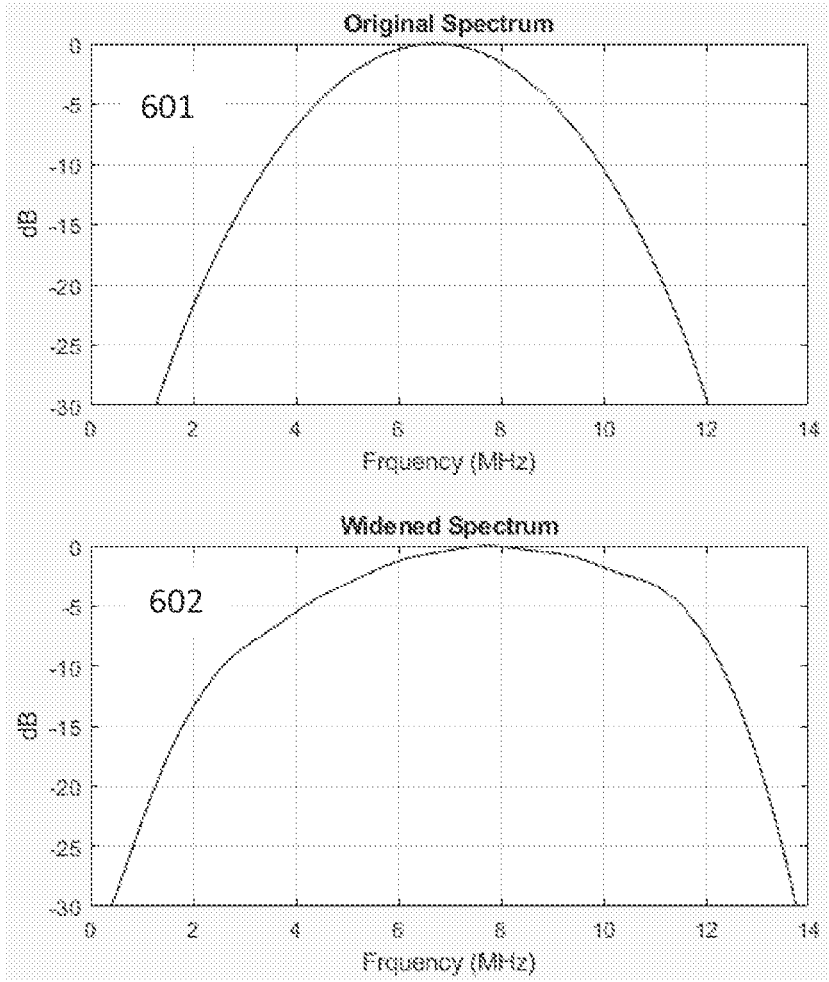
FIG. 6 shows an exemplary original spectrum and an exemplary widened spectrum for an ultrasound transducer.

For example, FIG. 6 shows an exemplary original spectrum 601, or simulated frequency response, of an ideal ultrasound transducer. The original spectrum 601 is symmetric and Gaussian, and the 6 dB relative bandwidth of the transducer is 77%, which results in limited axial resolution. However, widening the effective bandwidth of the transducer improves axial resolution. For example, the widened spectrum 602 shown in FIG. 6 illustrates a widened frequency response for a transducer with a 6 dB relative bandwidth of 102%, showing a 32% increase over the original bandwidth. Because axial resolution of an acoustic image is directly related to a relative bandwidth of the transducer spectrum, a 32% increase in relative bandwidth of the transducer spectrum can improve axial resolution by about 32%. The methods and systems presented herein uses NLFM chirp waveforms to broaden bandwidth of transmitted acoustic signals (e.g., transmitted by an ultrasound probe).

Figure 1:
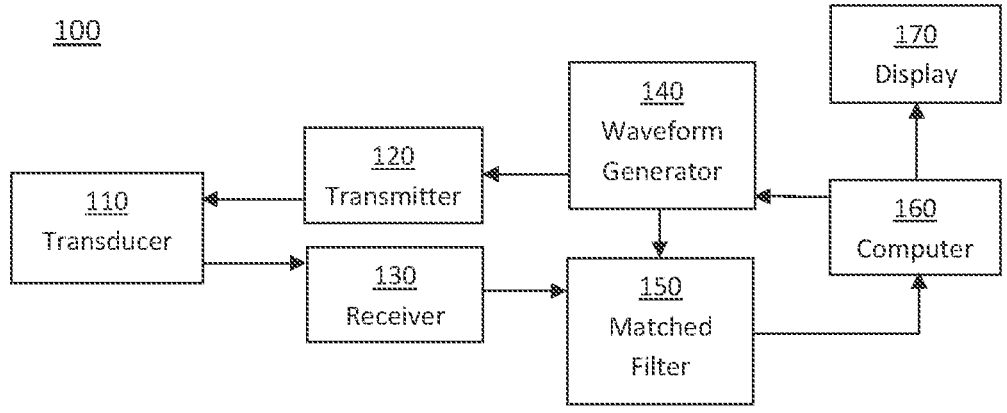
FIG. 1 is a block diagram of an exemplary acoustic imaging system for acoustic imaging based on windowed nonlinear frequency modulation (NLFM) chirp signals.

FIG. 1 is a block diagram of an exemplary acoustic imaging system 100 capable of generating windowed nonlinear frequency modulation (NLFM) chirp signals. The acoustic imaging system 100 includes a transducer 110, a transmitter 120, a receiver 130, a waveform generator 140, a matched filter 150, a computer 160, and a display 170. The waveform generator 140 may generate and then send digital waveforms to the transmitter 120 and/or the matched filter 150. The transmitter 120 may convert the digital waveforms into electrical signals (high voltage electrical signals) to excite transducer elements of the transducer 110. In some implementations, the transmitter 120 may include a bipolar transmitter(s), and/or a multilevel transmitter(s). In some implementations, the transmitter may include custom-built transmitters (e.g., for generating continuous signals). The transducer 110 may include, for example, a piezoelectric sensor, a single crystal material sensor, a piezoelectric micromachined ultrasound transducer (PMUT), a capacitive micromachined ultrasonic transducer (CMUT) sensor, and/or the like. The transducer 110 may convert the electrical signals into acoustic signals during a transmit phase and inversely convert detected acoustic echoes back to electrical domain by generating imaging signals during a receive phase. The receiver 130 may process the detected echo signals and convert them from analog signals to digital signals. The matched filter 150 may use the waveforms received from the waveform generator 140 to produce a set of coefficients of a filter that compresses the imaging signals after the imaging signals are digitized by the receiver 130. The computer 160 may be configured to perform various tasks including data management, signal and image processing, user interfacing, and/or the like. The display 170 may be operatively coupled to the computer 160 and show ultrasound images (e.g., real-time ultrasound images) and other relevant information (e.g., a set of information processed by the computer 160 about the ultrasound image) for the user to make diagnostic observations and decisions. A connection between the computer 160 and the display 170 may be through a wired electrical medium (e.g., High Definition Multimedia Interface (HDMI), Digital Visual Interface (DVI), Video Graphics Array (VGA), and/or the like) and/or a wireless electromagnetic medium (e.g., WIFI™, Bluetooth®, and/or the like), and/or the like. The acoustic imaging system 100 may generate windowed NLFM chirp signals.

In some implementations, the acoustic imaging system 100 may include or be operatively coupled to additional components not shown in FIG. 1. For example, the acoustic imaging system 100 may be operatively coupled to peripheral components such as, for example, a keyboard user interface, a color printer, a storage device, a foot switch, a video camera, and/or the like. A connection between each peripheral component and the acoustic imaging device 100 may be via a wired and/or a wireless medium.

In some variations, one or more elements or devices of the acoustic imaging system may be integrated or combined. In one example, the display 170 and the computer 160 may be combined in a computing device that includes a display screen (e.g., a laptop, a phone, and/or the like). In another example, the waveform generator 140 and the computer 160 may be integrated into a device that generates signals for the transmitter 120 and analyzes the imaging signals received from the matched filter 150. In some variations, the computer 160 may be replaced by a general purpose central processing unit (CPU)-based computer, a powerful (graphical processing unit) GPU-based computer, a specialized digital signal processing (DSP)-based device, a combination of those, and/or any other suitable computing systems.

In some variations, the system 100 may include at least one optical sensor (e.g., a whispering gallery mode optical sensor, an integrated photonic circuit based optical sensor, and/or the like) for receiving the acoustic echoes (in addition or as an alternative to the transducer 110 receiving the acoustic echoes). The at least one optical sensor may convert the set of echo signals to a set of optical signals, and the set of imaging signals may be generated based on the set of optical signals.

The at least one optical sensor may be configured to receive and detect echo signals with high sensitivity and broad bandwidth response. The at least one optical resonator may be similar to any of the optical resonators described in International Patent App. No. PCT/US2020/064094 and/or International Patent App. No. PCT/US2021/022412, each of which is incorporated herein in its entirety by this reference.

In some variations, the system may include a mixed array of at least one optical sensor and at least one transducer 110. The mixed array may be similar to any of the mixed arrays described in International Patent App. No. PCT/US2021/033715, which is incorporated herein in its entirety by this reference. In some variations, the mixed array may be used to perform harmonic imaging as described in International Patent App. No. PCT/US2021/039551, which is incorporated herein in its entirety by this reference. In some variations, signals from the mixed arrays may be combined or otherwise processed through a synthetic aperture technique and/or image compounding technique, such as techniques described in International Patent App. Nos. PCT/US2021/049226 and/or PCT/US2021/056096, each of which is incorporated herein in its entirety by this reference.

Figure 2:
FIG. 2 is a flowchart showing an exemplary method of acoustic imaging.

FIG. 2 is a flowchart showing an exemplary method 200 of acoustic imaging. In some implementations, an acoustic imaging system (such as the acoustic imaging system 100 as shown and described with respect to FIG. 1) may be used to perform the method 200. At 201, a nonlinear frequency modulation (NLFM) chirp waveform is generated based on a frequency response of at least one transducer. The NLFM chirp waveform may be generated based on a function that is non-decreasing, positive, and continuous. For example, the function may be based on an arctangent function, a polynomial function, or based on a lookup table. In some implementations, the NLFM chirp waveform may be predetermined and stored in a memory (not shown) of a waveform generator (e.g., the waveform generator 140 as shown and described with respect to FIG. 1) and/or stored in a memory (not shown) of a computer (e.g., the computer 160 as shown and described with respect to FIG. 1). In some implementations, the NLFM chirp waveform may be determined dynamically (e.g., on the fly). For example, a set of parameters of an NLFM chirp waveform function may be adjusted in real-time or near real-time based on an image that is being generated at the acoustic imaging system, as further described below.

Figure 7:
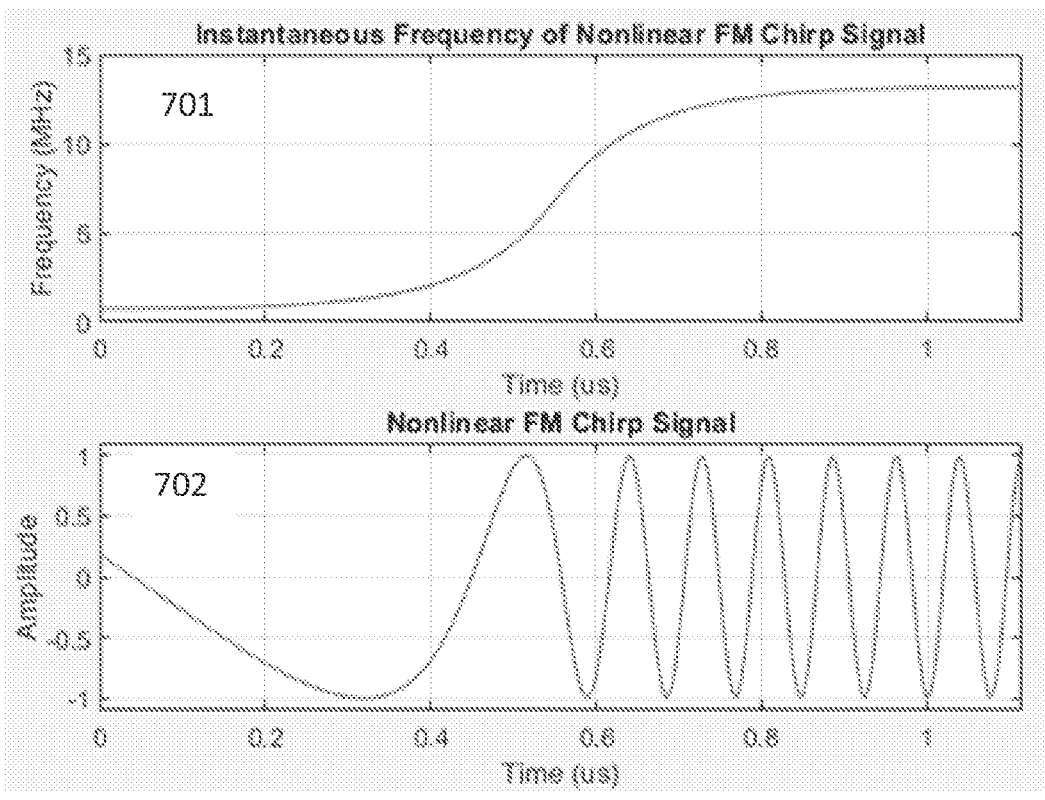
FIG. 7 shows an exemplary frequency distribution and an exemplary waveform of an NLFM chirp signal.

FIG. 7 shows an exemplary NLFM chirp waveform 702 and an exemplary frequency distribution 701 of the NLFM chirp waveform as a function of time. As shown in the frequency distribution 701 of the NLFM chirp waveform, the frequency increases monotonically, but not linearly, with time. The frequency increases very slowly starting from 0.71 MHz until around time 0.4 microsecond (μs). Between time 0.4 μs and the middle point on the time axis, at 0.55 μs, the frequency increases quickly. After the middle point on the time axis, however, the frequency increases at a slower pace up until time 0.7 μs. The frequency increases very slowly once again after 0.7 μs before reaching the maximum frequency value of 13.4 MHz. The NLFM chirp waveform 702 is also shown. The frequency increment rate in the NLFM chirp waveform 702 increase with time at the same pace as the frequency distribution 701. The waveform varies with time slowly in the beginning, then starts to vary more quickly before reducing the frequency increment rate as also seen in the frequency distribution curve 701. The waveform of the NLFM chirp signal may result in a concave-shaped spectrum. Exciting ultrasound transducers by an electrical signal with such a concave-shaped spectrum can increase the relative bandwidth of transmitted acoustic signals as shown and described with respect to FIG. 6. The wideband echo signals generated based on the NLFM chirp waveform may be compressed to generate images with improved axial resolution using the matched filter, as described above.

Figure 8:
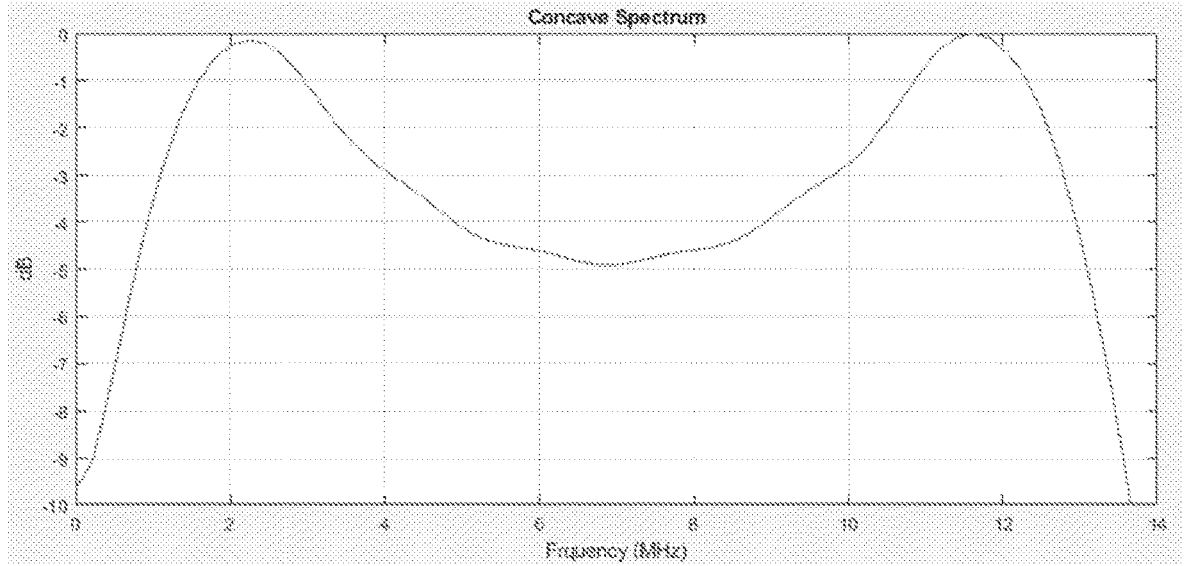
FIG. 8 shows an exemplary concave-shaped spectrum calculated from an NLFM chirp signal.

FIG. 8 shows an exemplary concave-shaped spectrum calculated from an NLFM chirp signal. The concave-shaped spectrum indicates that the chirp signal can enhance frequencies near 2 and 11 MHz by about 5 dB relative to the center frequency 7 MHz. The local minimum is around the center frequency as shown in the FIG. 8. If a 7 MHz transducer can be modelled as a linear time-invariant system, the output spectrum of the transducer excited by an NLFM chirp signal may be expressed as a sum of the frequency response of the transducer and the spectrum of the chirp signal in logarithmic scale. Therefore, a resulting transmitted acoustic signal based on the NLFM chirp signal can have a wider bandwidth than the original or intrinsic transducer bandwidth because of signal strength enhancement on both low and high frequency ends.

The concept shown and described in FIGS. 7 and 8 may be extended to cover transducers with different center frequencies, bandwidths, and spectral shapes. In some instances, for example, center frequencies may be higher than 7 MHz or lower than 7 MHz, bandwidths may be lower or higher than 77%. In some instances, for example, spectral shapes may be non-Gaussian or non-symmetric. For different transducers different frequency distributions (e.g., different from the frequency distribution 701) may be used to optimize transmitted acoustic signals in terms of bandwidth and spectral shape.

Figure 9:
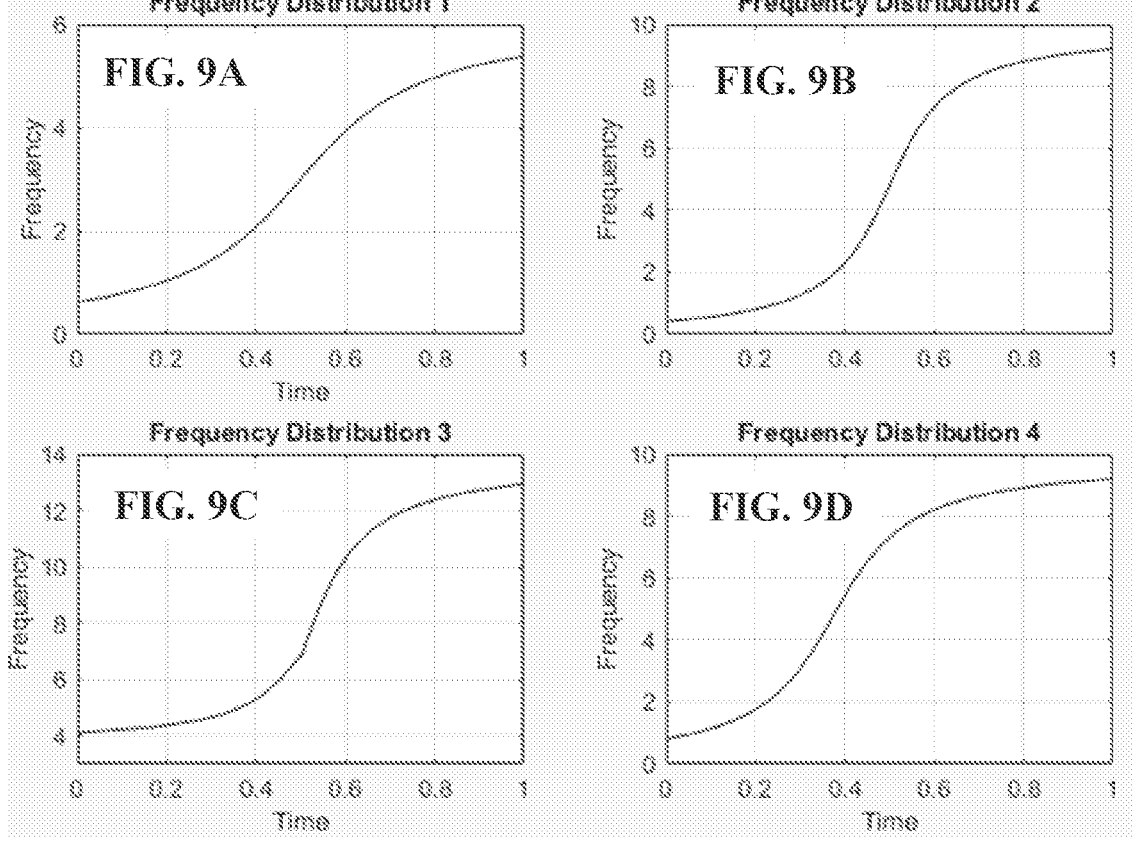
FIGS. 9A-9D show exemplary frequency distributions for NLFM chirp signal generation.

FIGS. 9A-9C show exemplary frequency distributions for NLFM chirp signal generation. The time scale is normalized for easy comparisons between the four frequency distributions. The frequency distribution of FIG. 9A shows an odd symmetric frequency distribution about the vertical line at the middle point 0.5 ranging from 0.63 MHz to 5.4 MHz. The frequency distribution of FIG. 9B shows another odd symmetric frequency distribution ranging from 0.43 MHz to 9.2 MHz. The frequency distribution of FIG. 9C shows an asymmetric frequency distribution ranging from 4.1 MHz to 12.9 MHz. The frequency distribution of FIG. 9D shows another asymmetric frequency distribution ranging from 0.84 MHz to 9.2 MHz.

A desired NLFM chirp waveform may be generated in any suitable manner. A first method to generate the desired NLFM chirp waveform is to use a function such as:

$$f(t) = c\, a\, \tan(a(t-b)) + d$$

where a tan( ) is the arctangent function, t is time ranging start time $T_0$ to finish time $T_1$, a is a positive scaling parameter, b is a real number determining the shift, c is a positive frequency range control parameter, and d is a positive number determining the initial minimum frequency. Other functions may also be used to generate NLFM chirp waveforms. More generally, any functions that meet the following three conditions may be used to generate NLFM chirp waveforms:

(a) The function is a non-decreasing function.

(b) The function is a positive function.

(c) The function is a continuous function.

In some variations, a second method to generate the desired NLFM chirp waveform is to use an n-th order polynomial function or other commonly used functions to approximate a function that satisfying the three above criteria. In some variations, a third method to generate the desired NLFM chirp waveform is to use look up tables (LUT) populated with predetermined data, in order to generate desired waveforms.

Any of the above-described methods for generating the desired NLFM chirp waveform (and/or other suitable methods therefor) may be performed either offline or online, and in any suitable combination. In the offline approach, some or all NLFM chirp waveforms are computed in a predetermined manner and then stored on one or more memory devices associated with the ultrasound imaging system. Such stored waveforms may be later accessed for use during operation of the ultrasound imaging system. In contrast, in the online approach, individual waveform(s) are computed and used by the ultrasound imaging system on the fly, such as according to imaging modes, operating frequencies, and/ or clinical applications.

Referring again to FIG. 2, at 202, an apodized signal may be generated by applying a window function to the NLFM chirp waveform. The signal generated at 201 based on the NLFM chirp waveform may introduce a sidelobe(s) having a magnitude. For example, an elevated range sidelobe level (RSLL) may have a magnitude at about −23 to −25 dB levels. Such RSLLs values can limit a performance of the method of acoustic imaging based on linear and/or nonlinear FM chirp signal excitation and can make application of linear and/or nonlinear FM chirp signal excitation less interesting for commercial ultrasound imaging methods. The window function (e.g., a Gaussian window function, a Kaiser window function, and/or the like) can advantageously reduce the magnitude of the sidelobe(s) that were introduced by the NLFM chirp waveform.

At 203, the at least one transducer (e.g., the transducer 110 as shown and described with respect to FIG. 1) is excited with the apodized signal, to induce the transducer 110 to emit an acoustic signal. Exciting the at least one transducer can be performed by a transmitter (e.g., the transmitter 120 as shown and described with respect to FIG. 1 and FIG. 3). In short, the transmitter can receive digital waveforms and beamformer control signals and excite the at least one transducer using a high voltage output amplifier. As is further described below, the acoustic signal emitted by the at least one transducer is generated based on the apodized signal (nonlinear frequency modulation (NLFM) chirp waveform and the window function) and may have wider bandwidth than the intrinsic bandwidth of the at least one transducer.

Figure 10:
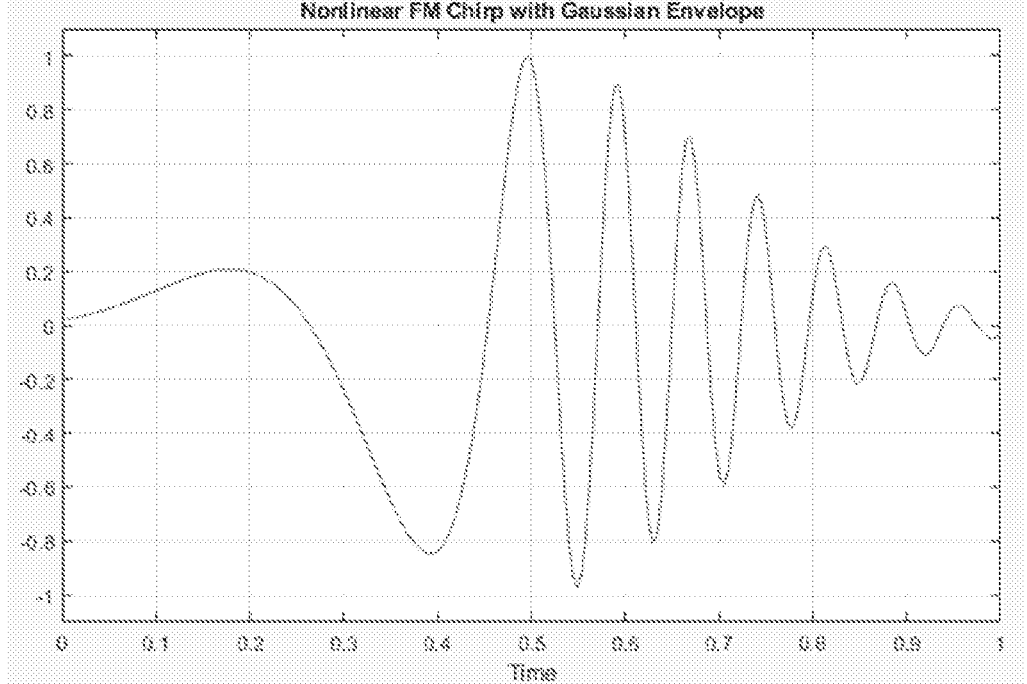
FIG. 10 shows an exemplary NLFM chirp waveform with Gaussian envelope.

FIG. 10 shows an exemplary NLFM chirp waveform with Gaussian window function. The waveform may be generated by multiplying an NLFM chirp signal with a Gaussian window function. The Gaussian window function is adjustable regarding its window width. Beside the Gaussian window function, other windows such as Kaiser windows can also be used to apodize NLFM chirp signals. Such windows are able to significantly reduce range sidelobe level (RSLL). Elevated RSLL reduces signal-to-noise ratio (SNR) and degrades axial resolution and contrast resolution of final ultrasound images.

The method 200 may optionally include receiving a set of echo signals in response to transmitting the acoustic signal, and generating a set of imaging signals based on the set of echo signals. In some implementations, the at least one transducer may receive the set of echo signals and generating the set of imaging signals. In some implementations, at least one optical sensor may receive the set of echo signals, convert the set of echo signals to a set of optical signals, and generate the set of imaging signals based on the set of optical signals (e.g., using a photodetector(s)). Images generated based on the set of imaging signals (resulting from excitation of the at least one transducer with the apodized signal as described above) may have an increased axial resolution of the image, an increased contrast resolution of the image, an increased signal-to-noise ratio of the image, and/or the like, compared to images generated without using the apodized signal.

The method 200 may optionally include delaying one or more imaging signals using one or more respective delay units in order to perform dynamic receive focusing. Such dynamic receive focusing functions to achieve overall, uniform image focusing by re-phasing imaging signals in accordance with each signal's travel distance (that is, re-phasing imaging signals in a depth-dependent manner), to avoid loss of resolution. The delay units may have a delay value calculated or determined based on a depth of focus value for imaging. The method 200 may further involve summing the set of imaging signals (after the delaying) to produce an output signal.

As described in further detail below, one or more matched filters may be applied to auto-correlate received echo or imaging signals with the same NLFM chirp waveform. In some variations, before the set of imaging signals are summed each of the set of imaging signals may be correlated with the NLFM chirp waveform using a respective matched filter to produce compressed imaging signals. Alternatively, instead of correlating each imaging signals separately, in some variations a similar correlation with the NLFM chirp waveform may be performed after summing; that is, the sum of the imaging signals may be correlated with the NLFM chirp waveform using a single matched filter.

It should be understood that the method 200 may include computer implemented processes (e.g., instructions stored in memory and executed on processors). Moreover, where methods described above indicate certain events occurring in certain order, the ordering of certain events may be modified. Additionally, certain of the events may be performed repeatedly, concurrently in a parallel process when possible, as well as performed sequentially as described above. Furthermore, certain embodiments can have one or more described events.

The acts performed at method 200 may be ordered in any suitable way. Accordingly, embodiments can be constructed in which processes or steps are executed in an order different than illustrated, which can include performing some steps or processes simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

Figure 3:
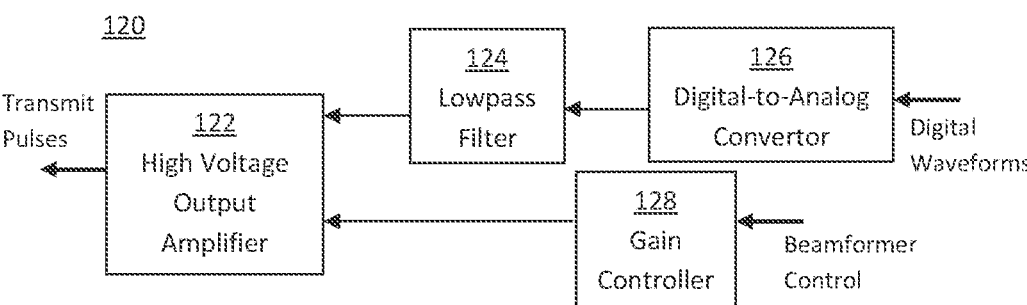
FIG. 3 is a block diagram of an exemplary transmitter.

FIG. 3 depicts a schematic of an exemplary transmitter 120 that may be used in the system 100 and/or method 200. As shown in FIG. 3, the transmitter 120 may include a high voltage output amplifier 122, a lowpass filter 124, a digital-to-analog converter (DAC) 126, and a gain controller 128. The DAC 126 and the gain controller 128 may receive digital waveform and beamformer control signals, respectively. The DAC 126 may convert digital waveforms generated by the waveform generator 140 into analog signals. The lowpass filter 124 may remove undesired high frequency components of the analog signals from the analog signals. The high voltage output amplifier 122 may then increase a power of the analog signals before outputting transmit signals that excite the transducer elements for generation of acoustic signals. On the other hand, the gain controller 128 may also adjust an amplitude of each individual transmit signal from the transmit signals for proper transmit channel apodization according to a set of beamformer control signals received at the gain controller 128. The set of beamformer control signals may be determined and received by a beamformer. In some implementations, the set of beamformer control signals may be determined and received from the computer 160 (e.g., the beam former being integrated into the computer 160). The transmit apodization may improve acoustic beam patterns and suppress sidelobes in lateral dimension.

Figure 4:
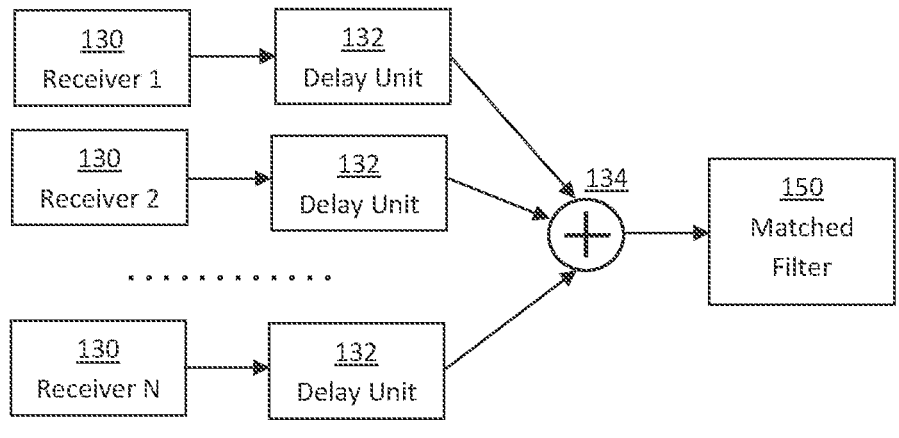
FIG. 4 is a block diagram of an exemplary receive beamformer.

FIG. 4 shows a block diagram of an exemplary receive beamformer in which dynamic receive focusing is performed prior to applying a matched filter that correlates the imaging signal(s) to the NLFM chirp waveform. The receive beamformer may process echo signals received at the transducer (e.g., a piezoelectric transducer, an optical sensor, and/or the like) in response to the transmitted acoustic signals (generated based on the NLFM chirp waveform and the window function). Additionally or alternatively, the receive beamformer may process optical signals corresponding to echo signals received as one or more optical sensors. The receive beamformer may include N receive channels. N is a positive integer that is often in the range of 2 to 512. In some implementations, the receive beamformer may include more than 512 receive channels. Each channel from the receive channel may include at least two components: a receiver 130 and a delay unit 132. The receiver 130 may perform several signal processing tasks such as signal amplification, time gain control (TGC), programmable gain amplification (PGA), anti-aliasing lowpass filtering (AALPF), analog-to-digital conversion (ADC), and/or the like. The delay units 132 may apply proper delay values to all the digitized echo signals before summing them together. The delay values are usually depth-dependent when performing dynamic receive focusing. In some implantations, the delay values can be determined or calculated based on a depth of focus value. The adder 134 can sum (e.g., a numerical summation of) all N channel data to produce a compressed output signal(s). In this example, the receive beamformer may operate using a single matched filter 150, which correlates the summed beamformer output (based on the echo signals) with the NLFM chirp waveform to compress the signal width and produce a compressed imaging signal(s). Using a single matched filter 150 as shown in FIG. 3 is a simple and/or cheap way to implement the receive beamformer.

Figure 5:
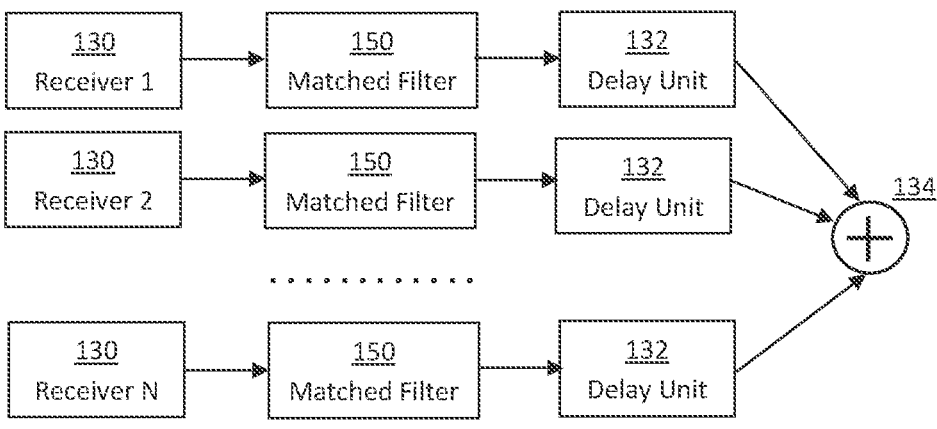
FIG. 5 is a block diagram of an exemplary receive beamformer.

FIG. 5 shows a block diagram of an exemplary receive beamformer in which dynamic receive focusing is performed after applying matched filters) to respective imaging signals. The receive beamformer may operate using a set of matched filters 150. The beamformer may include a set of receive channel (e.g., N receive channels, N being a positive integer between 2 and 512). Each channel from the set of receive channels may include three components: a receiver from a set of receivers 130, a matched filter from a set of matched filters 130, and a delay unit from a set of delay units 132. The receiver 130 may perform several signal processing tasks including signal amplification, time gain control (TGC), programmable gain amplification (PGA), anti-aliasing lowpass filtering (AALPF), analog-to-digital conversion (ADC), and/or the like. Each respective matched filter from the set of matched filters 150 may correlate a digitized signal produced by a respective receiver from the set of receivers 130 with the NLFM chirp waveform, to generate a compressed output signal(s). The delay units may apply proper delays to the compressed echo signals before summing them together. The delay values are usually depth-dependent when performing such dynamic receive focusing. The adder 134 may sum all signal received from each channel of the set of receive channel to produce a compressed imaging signal(s). Although implementing the receive beamformer using the set of matched filters 150 can be more complicated and expensive compared to implementing the receive beamformer using a single matched filter, an overall imaging performance (image quality) may be improved by using the set of matched filters. It should be understood that the receive beamformers shown in FIGS. 4 and 5 are exemplary in nature, and in other embodiments the system (e.g., a receive beamformer) may include one or more receivers, one or more delay units, and/or one or more matched filters in any suitable combination. For example, in some embodiments, signals from a first portion of the system's receive channels may be arranged similar to that shown in FIG. 4, while a second portion of the system's receive channels may be arranged similar to that shown in FIG. 5.

Figures 11A, 11B, 11C, 11D, 11E, 11F, 11G, 11H:
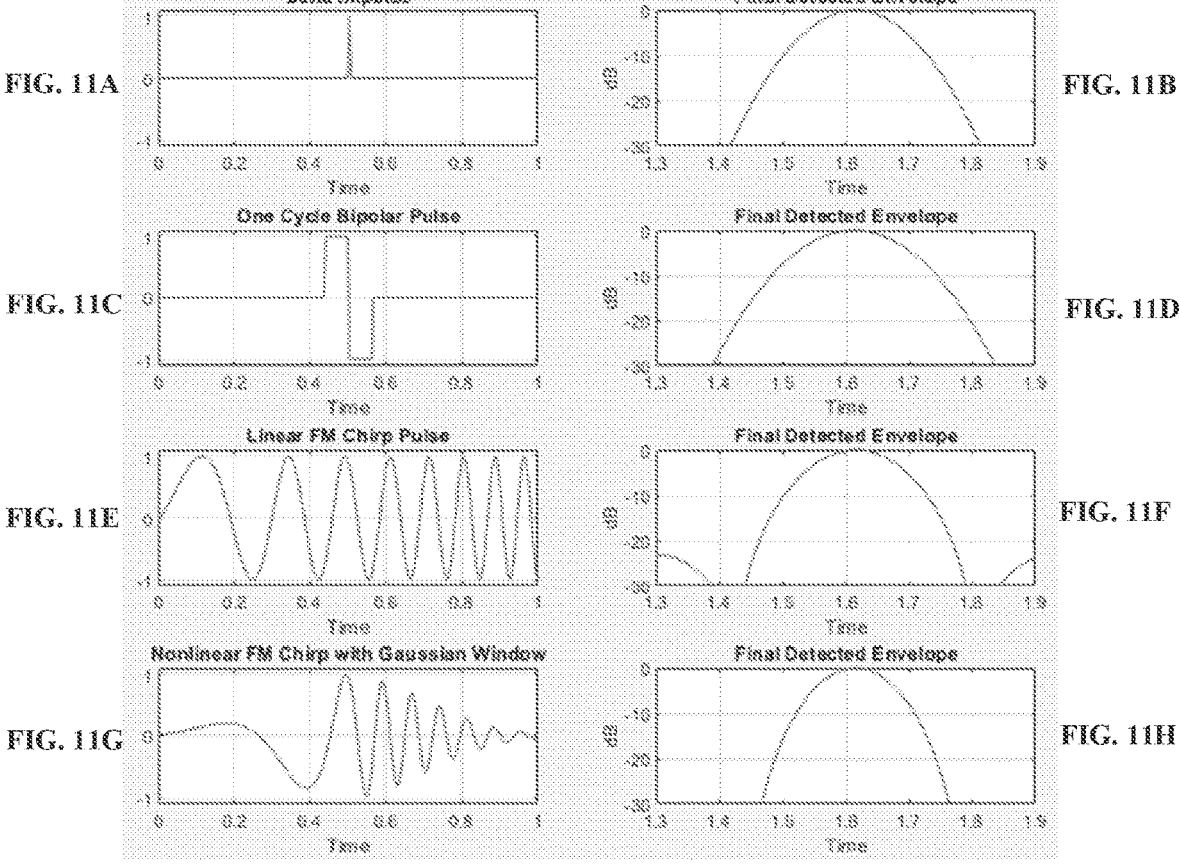
FIGS. 11A-11H show exemplary excitation signals and respective detected envelopes based on the excitation signals.

The methods and devices of acoustic imaging described herein can generate acoustic images with improved axial resolution based on exciting transducers that transmit acoustic waves by the windowed NLFM chirp signal. Moreover, the generated images have reduced or no RSLL compared to images produced by known methods and devices of acoustic imaging. For example, FIGS. 11A-11H show various exemplary excitation signals (including an exemplary windowed NLFM chirp signal) and respective detected envelopes based on the excitation signals for comparison. The excitation signals include a delta impulse (FIG. 11A), a one cycle bipolar pulse (FIG. 11C), a linear FM chirp signal (FIG. 11E), and an NLFM chirp signal with Gaussian window (FIG. 11G). More specifically, FIG. 11A, FIG. 11C, FIG. 11E, and FIG. 11G respectively show a waveform of the delta impulse in time domain, a waveform of the one cycle bipolar pulse in time domain, a waveform of the linear FM chirp signal in time domain, and a waveform of the NLFM chirp signal with Gaussian window in time domain. FIG. 11B, FIG. 11D, FIG. 11F, and FIG. 11H respectively show a detected envelope based on the delta impulse, a detected envelope based on the one cycle bipolar pulse, a detected envelope based on the linear FM chirp signal, and a detected envelope based on the NLFM chirp signal with Gaussian window. The detected envelopes of FIG. 11B, FIG. 11D, FIG. 11F, and FIG. 11H go through the entire transmit and receive signal chain of an ultrasound imaging system (e.g., the acoustic imaging system 100 as shown and described with respect to FIG. 1).

The detected envelopes of FIG. 11B, FIG. 11D, FIG. 11F, and FIG. 11H may directly determine an axial resolutions, signal-to-noise ratios (SNR), and/or contrast resolutions of images generated based on the excitation signals of FIG. 11A, FIG. 11C, FIG. 11E, and FIG. 11G. As shown in FIGS. 11A-11H, the NLFM chirp signal with Gaussian window generates the narrowest envelope at all dB levels. Therefore, imaging based on an excitation signal using the NLFM chirp signal with Gaussian window FIG. 11G would generate an image with the best quality, compared to images generated based on excitation signals of 11A, 11C, or 11E. On the other hand, an image generated based on an excitation signal using the single cycle signal would be comparatively the worst in terms of envelope width. Although an image generated based on an excitation signal using the delta signal would be slightly better than the image generated based on the excitation signal using the single cycle signal, it shows theoretical resolution limit in comparison to the chirp signals. Using the delta signal on itself as excitation signal would be impractical due to its poor SNR performance.

Despite producing an excellent axial resolution, the linear FM chirp signal may have an elevated range sidelobe level (RSLL), such as at about −23 dB to −25 dB levels as shown in FIG. 11F. Such high RSLLs ultimately limit a performance of the linear FM chirp signal excitation technology and can make them less interesting for commercial ultrasound imaging systems. Therefore, based on the comparison results shown and described with respect to FIGS. 11A-11H, generating acoustic images (e.g., medical ultrasound images) based on the windowed NLFM chirp signal with Gaussian window can significantly improve axial resolution of the acoustic images without introducing high RSLL for medical ultrasound imaging systems.

Although the methods and systems described herein have been primarily described in the context of ultrasound imaging, in some variations, the methods and systems described herein can be used in applications other than ultrasound imaging. For example, in some instances, the methods and systems described herein may be used in metrology, signal processing, particle physics, remote sensing, aerospace applications, and/or the like.

Figure 12:
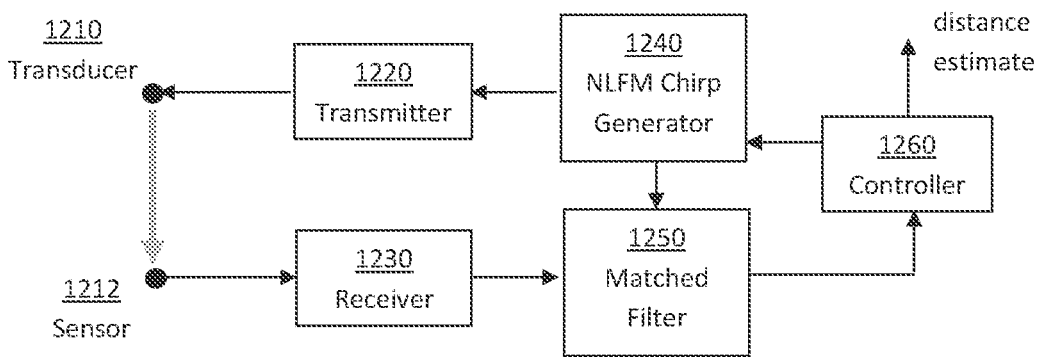
FIG. 12 shows an illustrative schematic of an exemplary ultrasound system configured to measure distance based on windowed NLFM chirp signals.

For example, the methods and systems described herein may be used for performing acoustic measurements such as distance measurements using NLMM chirp signals. FIG. 12 depicts an illustrative schematic of an exemplary acoustic system 1200 for performing distance measurements using NLFM chirp signals. The acoustic system 1200 may include a transducer 1210, a sensor 1212, a transmitter 1220, a receiver 1230, a waveform generator 1240, a matched filter 1250, and a controller 1260. In some implementations, the acoustic system 1200 may be configured to measure a distance between the transducer 1210 and the sensor 1212.

The transducer 1210 and/or the sensor 1212 may, in some variations, each be arranged in a respective array of transducers and/or sensors. The transducer 1210 and sensor 1212 need not be in the same physical apparatus, but instead may, in some variations, be arranged in separate physical apparatuses positioned apart and configured to communicate signals directly or indirectly to the same controller 1260 (or multiple controllers in communication with each other). For example, the transducer 1210 may be arranged in a first probe and the sensor 1212 may be arranged in a second probe, where one or both of the probes may be manipulated and/or positioned as desired locations between which the distance is to be measured. As another example, the transducer 1210 and/or the sensor 1212 may be arranged in an item such as a needle (or endoscope, catheter, etc.) whose position is desired to be located and/or tracked, such as during a medical procedure, such that the relative locations of the of the transducer 1210 and/or the sensor 1212 may be measured (in real-time or near-real time, or periodically, etc.) so as to locate and/or track the item.

In a process similar to that described above with respect to FIG. 2, the waveform generator 1240 may generate and send digital waveforms to the transmitter 1220 and/or the matched filter 1250. Waveforms generated by 1240 may be an NLFM chirp signal, which may be apodized by applying a window function to the NLFM chirp signal. The transmitter 1220 may convert the received digital waveforms into electrical signals (e.g., high voltage electrical signals) that excite the transducer 1210.

Similar to the transducer 110 described above with respect to FIG. 1, the transducer 1210 may include a piezoelectric transducer, a single crystal material transducer, a PMUT, a CMUT, and/or other suitable transducer configured to convert received electrical signals into acoustic signals that propagate in media. The sensor 1212 (e.g., optical sensor such as WGM resonator or other resonator, interferometer, or piezoelectric sensor) may detect the acoustic signals emitted by the transducer 1210 and then convert these measurement signals back into an electrical domain.

In a process similar to that described above, the receiver 1230 may process the detected electrical signals and convert them from analog signals to digital signals. The matched filter 1250 may use the waveforms received from the waveform generator 1240 to produce a set of coefficients of a filter that compresses the measurement signals after the measurement signals are digitized by the receiver 1230. The controller 1260 may be configured to perform various tasks including system control management, signal processing, user interfacing, and/or the like. The final output of the system is an estimated distance between the transducer 1210 and the sensor 1212.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A method for performing acoustic measurements comprising:

generating a nonlinear frequency modulation (NLFM) chirp waveform based on a frequency response of at least one transducer;

generating an apodized signal by applying a window function to the NLFM chirp waveform;

exciting the at least one transducer with the apodized signal, the at least one transducer transmitting a set of acoustic signals in response to excitation by the apodized signal, wherein at least one optical sensor receives one or more acoustic signals to obtain a set of received acoustic signals and generates a set of measurement signals based on the set of received acoustic signals, the at least one transducer being arranged in a probe, the at least one optical sensor being separate from the at least one transducer and being arranged in an item whose position is to be located and tracked during a medical procedure, the at least one optical sensor and the item being inside a patient body during the medical procedure; and determining a distance between the at least one optical sensor and the at least one transducer based on the set of measurement signals during the medical procedure.

2. The method of claim 1, wherein the set of acoustic signals have a higher bandwidth than an intrinsic bandwidth of the at least one transducer.

3. The method of claim 1, further comprising:

receiving by the at least one transducer a plurality of echo signals in response to transmitting by the at least one transducer the set of acoustic signals; and generating a plurality of imaging signals based on the plurality of echo signals.

4. The method of claim 3, wherein receiving the plurality of echo signals further comprises receiving at least one echo signal using the at least one optical sensor, and wherein generating the plurality of imaging signals comprises converting the at least one echo signal to an optical signal, and generating the plurality of imaging signals based on the optical signal.

5. The method of claim 3, further comprising:

delaying one or more imaging signals of the plurality of imaging signals using one or more respective delay units; and summing the plurality of imaging signals to produce an output signal.

6. The method of claim 5, further comprising:

after summing the plurality of imaging signals, correlating the output signal with the NLFM chirp waveform using a matched filter, to produce a compressed output signal.

7. The method of claim 5, further comprising:

before summing the plurality of imaging signals, correlating each of the plurality of imaging signals with the NLFM chirp waveform using a respective matched filter to produce compressed imaging signals; and wherein summing the plurality of imaging signals comprises summing the compressed imaging signals using an adder to produce the output signal.

8. The method of claim 5, wherein each delay unit is based on a depth associated with the imaging signal to be delayed by the delay unit.

9. The method of claim 3, wherein excitation of the at least one transducer with the apodized signal increases one or more of an axial resolution, a contrast resolution, and a signal-to-noise ratio of an ultrasound image generated based on the plurality of imaging signals.

10. The method of claim 1, wherein at least one of the NLFM chirp waveform and the window function is predetermined prior to performing the acoustic imaging.

11. The method of claim 1, wherein at least one of the NLFM chirp waveform and the window function is dynamically adjusted while performing the acoustic imaging.

12. The method of claim 1, wherein the NLFM chirp waveform is generated based on a function that is nondecreasing, positive, and continuous.

13. The method of claim 12, wherein the function is:

$$f(t)=c\,a\,\tan(a(t-b))+d$$

where a tan(•) is the arctangent function, t is time, a is a scaling parameter, b is a shift control parameter, c is a frequency range control parameter, and d is an initial minimum frequency parameter.

14. The method of claim 1, wherein the window function is a Gaussian window function or a Kaiser window function.

15. The method of claim 1, wherein the at least one transducer includes a piezoelectric sensor, a single crystal material sensor, a piezoelectric micromachined ultrasound transducer (PMUT), or a capacitive micromachined ultrasonic transducer (CMUT) sensor.

16. A system for acoustic measurements comprising:
at least one transducer arranged in a probe;
a non-transitory processor-readable medium storing code representing instructions to be executed by a processor of a first computing device, the code comprising code to cause the processor to generate a nonlinear frequency modulation (NLFM) chirp waveform based on a frequency response of the at least one transducer; and
a transmitter configured to:
generate an apodized signal based on the NLFM chirp waveform and a window function, and
excite the at least one transducer with the apodized signal;
the at least one transducer configured to transmits a set of acoustic signals in response to excitation by the apodized signal,
at least one optical sensor separate from the at least one transducer and arranged in an item whose position is to be located and tracked during a medical procedure, the at least one optical sensor and the item being inside a patient body during the medical procedure, the at least one optical sensor configured to:
receive one or more acoustic signals to obtain a set of received acoustic signals; and
generate a set of measurement signals based on the set of received acoustic signals; and
the non-transitory processor-readable medium further comprising code to cause the processor to determine a distance between the at least one optical sensor and the at least one transducer based on the set of measurement signals during the medical procedure.

17. The system of claim 16, further comprising:
the at least one optical sensor configured to receive at least one echo signal and convert the at least one echo signal to an optical signal; and
at least one photodetector configured to generate a plurality of imaging signals based on the optical signal.

18. The system of claim 17, further comprising:
one or more respective delay units configured to delaying one or more respective imaging signals of the plurality of imaging signals; and
an adder configured to produce an output signal based on the plurality of imaging signals.

19. The system of claim 18, further comprising a matched filter configured to, after summing the plurality of imaging signals, correlate the output signal with the NLFM chirp waveform.

20. The system of claim 18, further comprising:
a plurality of matched filters configured to correlating the plurality of imaging signals with the NLFM chirp waveform to produce compressed imaging signals,
wherein the adder is configured to sum the compressed imaging signals to produce the output signal.

21. The system of claim 18, wherein the non-transitory processor-readable medium further comprising code to:
calculate a plurality of delay values for the one or more respective delay units, based on a depth of focus value.

22. The system of claim 16, wherein the window function is a Gaussian window function or a Kaiser window function.

23. The system of claim 16, wherein the at least one transducer includes a piezoelectric sensor, a single crystal material sensor, a piezoelectric micromachined ultrasound transducer (PMUT), or a capacitive micromachined ultrasonic transducer (CMUT) sensor.

24. The method of claim 1, further comprising receiving at least one acoustic signal using a second transducer different from the excited transducer.

25. The method of claim 1,
wherein receiving the one or more acoustic signals comprises receiving at least one acoustic signal using the at least one optical sensor, and
wherein generating the set of measurement signals comprises converting received acoustic signals to a plurality of optical signals, and generating the set of measurement signals based on the plurality of optical signals.

26. The method of claim 1, further comprising:
correlating at least one of the set of measurement signals with the NLFM chirp waveform using a matched filter, to produce a compressed measurement signal.

27. The method of claim 1, wherein at least one of the NLFM chirp waveform and the window function is predetermined prior to performing the acoustic measurements.

28. The method of claim 1, wherein at least one of the NLFM chirp waveform and the window function is dynamically adjusted while performing the acoustic measurements.

29. The method of claim 1, wherein the item comprises a needle, a catheter, or an endoscope.

30. The method of claim 1, wherein a frequency of the set of acoustic signals is in a range between 1 MHz and 14 MHz.

* * * * *